United States Patent [19]

Ito et al.

[11] Patent Number: 5,496,563
[45] Date of Patent: Mar. 5, 1996

[54] DRY GEL COMPOSITION

[75] Inventors: Yoji Ito; Yasuo Hirai, both of Tokyo, Japan

[73] Assignee: Showa Yakuhin Kako Co., Ltd., Tokyo, Japan

[21] Appl. No.: 196,070

[22] PCT Filed: Aug. 28, 1992

[86] PCT No.: PCT/JP92/01097

§ 371 Date: Feb. 28, 1994

§ 102(e) Date: Feb. 28, 1994

[87] PCT Pub. No.: WO93/04670

PCT Pub. Date: Mar. 18, 1993

[30] Foreign Application Priority Data

Aug. 30, 1991 [JP] Japan ................. 3-220435

[51] Int. Cl.$^6$ .................. A61K 9/14; A61K 47/36
[52] U.S. Cl. .................. 424/489; 424/439; 514/778; 514/944
[58] Field of Search ..................... 424/439, 488, 424/489; 514/778, 781, 944

[56] References Cited

U.S. PATENT DOCUMENTS

| | | | |
|---|---|---|---|
| 4,009,268 | 2/1977 | Cardon et al. | 424/180 |
| 5,147,655 | 9/1992 | Ibsen | 424/489 |
| 5,262,167 | 11/1993 | Vegesna et al. | 424/439 |
| 5,306,506 | 4/1994 | Zema et al. | 424/466 |
| 5,374,659 | 12/1994 | Gowan, Jr. | 514/557 |

Primary Examiner—Thurman K. Page
Assistant Examiner—James M. Spear
Attorney, Agent, or Firm—Oblon, Spivak, McClelland, Maier & Neustadt

[57] ABSTRACT

There is provided a dry gel composition comprising 40% by weight or below of a medicine which can be orally administered, 3% by weight or above of a gelling agent and 5% by weight or below of a binder, which composition is capable of forming a gruel-like aqueous gel composition upon mixing with 2 to 15 parts by weight of water per part by weight of the composition at a temperature of 40° C. or below. The gelling agent usable herein is, for example, pregelatinized starch having a concentration of 50% by weight or above. The medicine which can be orally administered is, for example, cinnarizine. Upon mixing with a predetermined quantity of water, the dry gel composition forms a homogeneous aqueous gel composition having a viscosity of about 100 to 500 cp, which is preferably thixotropic. Even aged people having a weak swallowing function can easily swallow the aqueous gel composition, without causing improper sucking into their tracheas. Thus, the dry gel composition of the present invention is very useful in their medical care. The aqueous gel composition can be prepared in a short time by an extremely simple operation at the time of use.

12 Claims, 3 Drawing Sheets

DRY GEL COMPOSITION

TECHNICAL FIELD

The present invention relates to a dry gel composition containing a medicine which can be orally administered and capable of forming a gruel-like gel composition upon mixing with a predetermined quantity of water at the time of use.

BACKGROUND OF THE INVENTION

As aged people are increasing in number in the population recently, there is a growing interest in their medical care. The swallowing function in the aged people is generally lower than that of younger healthier people, and it is not easy for them to swallow solid preparations such as tablets and capsules. Thus, it has been usually difficult to administer medicines, which are similar to those to be given to people in the prime of life, to the aged people. In the medical treatment of the aged people, the patients often have two or more diseases to be treated and usually two or more kinds of medicines including the solid preparations are prescribed for them. Thus, the swallowing of the medicines having different shapes often caused much labor and pain for them. It was proposed under these circumstances to administer a liquid preparation such as a syrup instead of the solid capsules in the pharmacotherapy of the aged people. However, the administration must be carefully carried out, since the reflective function in the bifurcation of trachea of the aged people is generally weak, and the liquid might be partially sucked in the trachea at the time of the swallowing. Particularly when an aged patient is nursed at home, serious problems such as dyspnea due to improper suction are often caused.

Therefore, the object of the present invention is to provide a composition from which a preparation which can be easily swallowed by aged people can be prepared at the time of use.

In particular, the object of the present invention is to provide a dry gel composition containing a medicine which can be orally administered and capable of rapidly forming an aqueous gel composition upon mixing with a predetermined quantity of water without heating at the time of use.

DISCLOSURE OF THE INVENTION

After intensive investigations made for the purpose of solving the above-described problems, the inventor has found that a gruel-like composition comprising a gel structure easily causes the swallowing reflex and, therefore, such a composition can be swallowed by even aged people having a weakened swallowing function without causing the improper suction in the trachea. The inventor has also found that the gel composition can be easily prepared from a dry gel composition containing a gelling agent capable of rapidly forming a gel upon mixing with water at 40° C. or below. The present invention has been completed on the basis of these findings.

Namely, the present invention provides a dry gel composition comprising 40% by weight or below, based on the whole composition, of a medicine which can be orally administered, 3% by weight or above of a gelling agent and 5% by weight or below of a binder, which composition is capable of forming an aqueous gruel-like gel composition upon mixing with 2 to 15 parts by weight of water per part by weight of the composition.

In an embodiment of the present invention, the dry gel composition comprises 40% by weight or below of a medicine which can be orally administered, 50% by weight or above of pregelatinized starch and 5% by weight or below of a binder, which composition is capable of forming an aqueous gruel-like gel composition upon mixing with 6 to 8 parts by weight of water per part by weight of the composition.

THE BEST EMBODIMENT FOR CARRYING-OUT THE INVENTION

When a specified quantity of water is added to the dry gel composition of the present invention and the resultant mixture is stirred at a temperature of 40° C. or below, preferably at 15° to 25° C., the composition is swollen, becomes bulky and forms an aqueous gel composition.

The term "gelation" generally indicates that colloidal particles dispersed in a dispersion medium are collected together by means of their affinity to form a secondary structure. The aqueous gel composition obtained by stirring the dry gel composition of the present invention with water has a structural viscosity. The aqueous gel composition preferably has thixotropic properties. The term "thixotropic properties" indicates such properties that when a mechanical stress is applied to the aqueous gel composition under isothermal conditions, its gel structure is broken to lower the viscosity but, after leaving the composition to stand for a while, the gel structure is regenerated to recover its viscosity. It is preferred that the aqueous gel composition is thixotropic since when the dry gel composition of the present invention is mixed with water in such a case, an intended aqueous gel composition is obtained with a high reproducibility irrespective of the mixing strength or mixing time.

Figure 1:
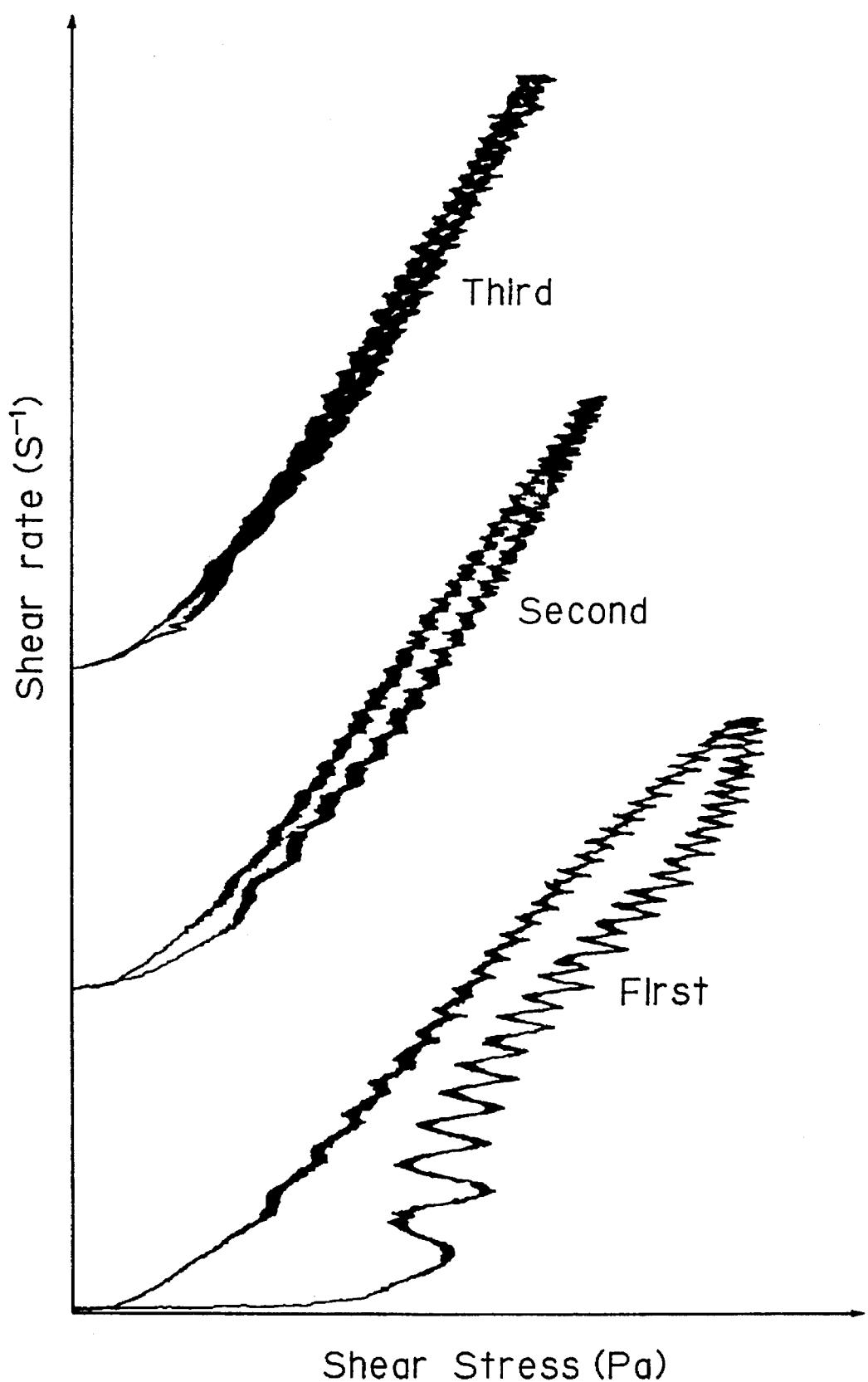
FIG. 1 shows a hysteresis curve obtained by mixing 1 part by weight of composition 7 given in Table 1 with 8 parts by weight of water, leaving the mixture to stand for 60 min and determining the relationship between shear stress of the aqueous gel composition and the shear rate with a cone plate-type rotational viscometer.
Figure 2:
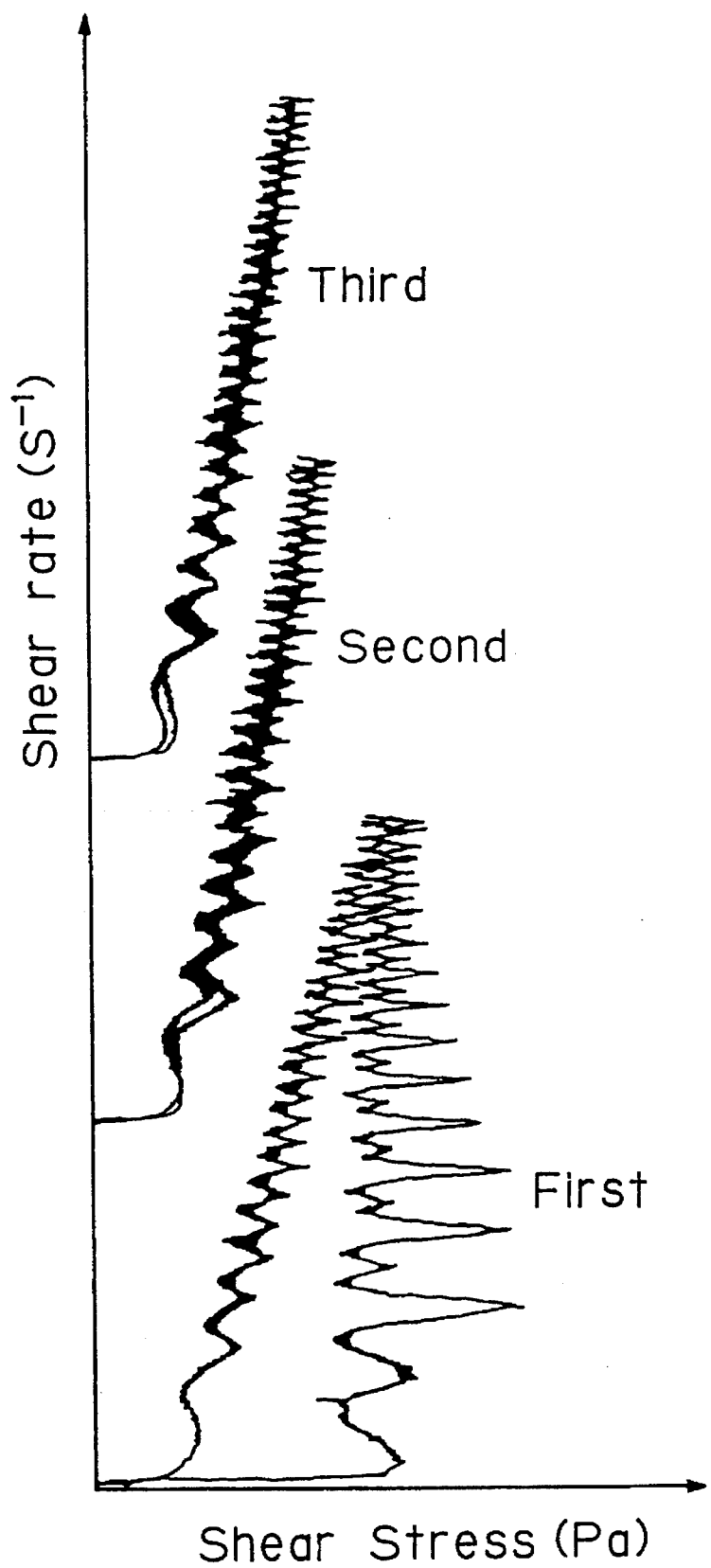
FIG. 2 shows a hysteresis curve obtained by mixing 1 part by weight of composition 6 given in Table 1 with 8 parts by weight of water, leaving the mixture to stand for 60 min and determining the relationship between shear stress of the aqueous gel composition and the shear rate with a cone plate-type rotational viscometer.

The properties of the aqueous gel composition obtained from the dry gel composition of the present invention can be determined by examining the relationship between the viscosity of the aqueous gel composition and the shear rate with, for example, a cone plate-type rotational viscometer and observing the change in the shear stress of the aqueous gel composition by the change in the stress from the hysteresis curve. Examples of the hysteresis curves of the aqueous gel compositions obtained from the dry gel compositions of the present invention are given in FIGS. 1 to 3.

Figure 3:
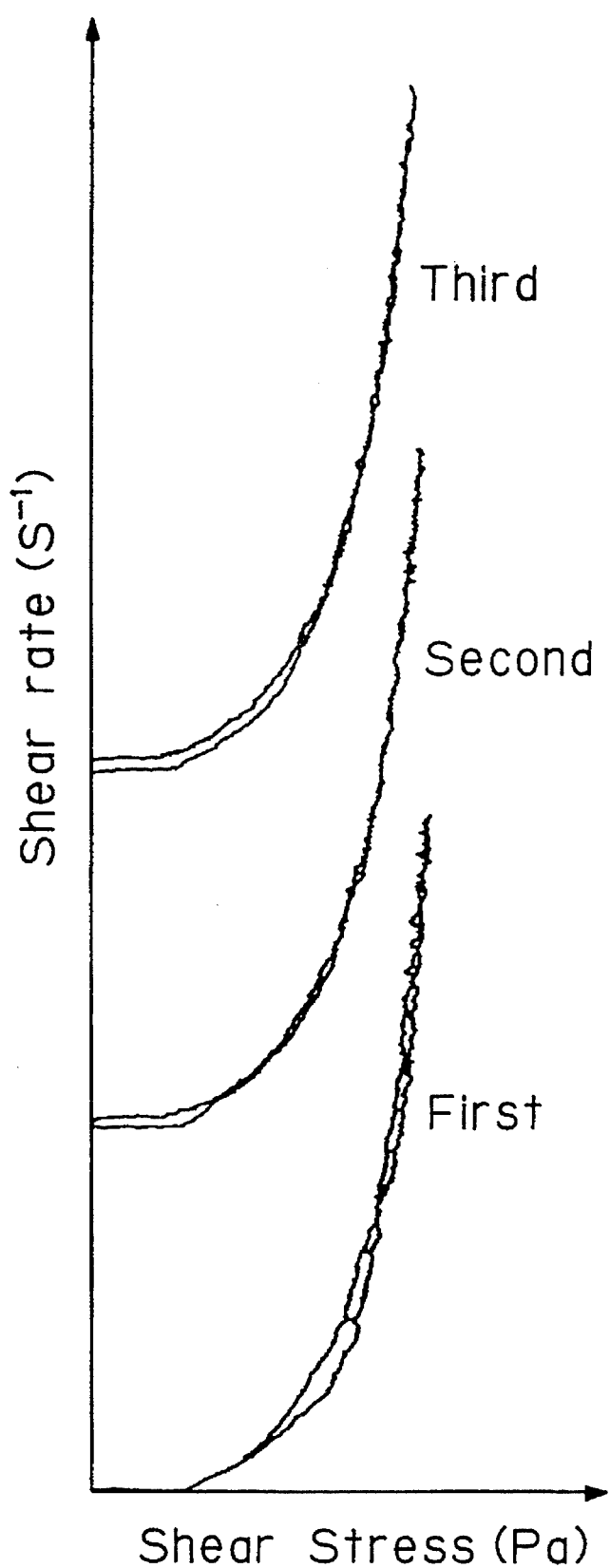
FIG. 3 shows a hysteresis curve obtained by mixing 1 part by weight of composition 12 given in Table 4 with 3 parts by weight of water, leaving the mixture to stand for 60 min and determining the relationship between shear stress of the aqueous gel composition and the shear rate with a cone plate-type rotational viscometer.

The fact that the flow curve representing the relationship between the rotation speed and torque rises as the rotation speed is elevated indicates that since the shear deformation speed of the sample is elevated as the rotation speed rises, the breaking of the structure in the aqueous gel composition is accelerated to lower the apparent viscosity. Thus, the higher the degree of the arching of the curve showing the hysteresis of the viscosity, the higher the degree of breaking of the gel structure by the mechanical stress. Therefore, it can be employed as an index of the degree of thixotropy. Where the gel structure broken as the rotation speed is reduced in the aqueous gel composition is not rapidly regenerated, the apparent viscosity is unchanged and, therefore, the area made by the hysteresis curve is large. Such an aqueous gel composition is preferred, since it keeps its fluidity even after the structure has been broken by mastication to make the swallowing easy. On the contrary, where the gel structure broken as the rotation speed is reduced in the aqueous gel composition is rapidly regenerated, the area made by the hysteresis curve is small. The properties of such an aqueous gel composition are shown in FIG. 3.

The gelling agent contained in the dry gel composition of the present invention is a substance which imparts the above-described properties to the dry gel composition of the present invention. In particular, the gelling agent is a substance which rapidly forms a gel upon mixing with water in a quantity of the maximum absorption or below at a temperature of 40° C. or below, preferably 15° to 25° C. The gelling agent is preferably a thixotrope, i.e. a substance capable of forming a thixotropic gel under the above-described conditions. The gelling agents which can be contained in the composition of the present invention include, for example, pregelatinized starch, sodium starch phosphate, carrageenin, locust bean gum, a mixture of carrageenin and locust bean gum, carboxymethylated starch, a mixture of LM pectin and a calcium ion-containing substance, or an acid substance, guar gum, a mixture of low substituted hydroxypropyl cellulose and sodium carboxymethyl cellulose, tragacanth powder, bentonite, a mixture of bentonite and sodium carboxymethyl cellulose, and a mixture of crystalline cellulose and sodium carboxymethyl cellulose. The gelling agents are not limited to them. Among them, pregelatinized starch is preferably used.

The term "pregelatinized starch" herein indicates a starch which forms no interference band in X-ray analysis. Pregelatinized starch can be prepared by, for example, a method wherein starch particles are heated together with water, a method wherein starch is treated with a swelling agent such as a calcium nitrate or sodium hydroxide solution, or a method wherein starch is etherified or esterified with phosphorus oxychloride. Pregelatinized starch prepared as described above can be dried at a temperature of, for example, 80° C. or above to reduce the water content thereof to 15% or below before the use. Still preferred pregelatinized starch used in the present invention is, for example, that prepared from corn starch by hot roll method. Such a product is available from, for example, Matsutani ChemicalsIndustries Co., Ltd. Such an pregelatinized starch has a water content of usually 13% by weight or below, preferably 10% by weight or below, and a particle size of 150 μm or below.

Other gelling agents usable in the present invention are also available on the market. For example, Pionil 1500 (a product of Matsutani Chemical Industries Co., Ltd.) is used as the sodium starch phosphate, GENU GEL SWG-J (a product of Copenhagen Pectin Factory) is used as the carrageenin; Primojel (a product of Matsutani Chemical Industries Co., Ltd.) is used. as the carboxymethylated starch; GENU pectin is used as the LM pectin, guaiacol is used as the guar gum; L-HPC(LH-31) and L-HPC(LH-21) are used as the low substituted hydroxypropyl cellulose; and Avicel RC-591NF is used as the mixture of crystalline cellulose and sodium carboxymethyl cellulose.

The medicine contained in the dry gel composition of the present invention is any of those which can be orally administered and dissolved and absorbed to exhibit its effect in the gastrointestinal tract. Examples of these medicines include antipyretic and analgesic agents such as ibuprofen and fenbufen; antivertigo agents such as betahistine and difenidol; neurotropic agents such as imipramine, amitriptyline, diazepam, haloperidol and timiperone; comprehensive cold remedies such as promethazine, saliycylamide, acetaminophen and anhydrous caffeine; medicines for central nerves such as idebenone; skeletal muscle relaxants such as dantrolene and chlorphenesin; antispastic agents such as afloqualone and eperisone; cardiotonic agents such as digitalis and digoxin; remedies for arrhythmia such as procaineamide, atenolol, pindolol and propranolol; diuretics such as hydrochlorothiazide and furosemide; hypotensive agents such as captopril, prazosin and methyldopa; vasodilator drugs such as dipyridamole, diltiazem, trapidil, nifedipine and isosorbide; medicines for diseases of the cardiovascular system such as vinpocetine, ifenprodil, pentoxifylline, nicardipine, cinnarizine and dihydroergotoxine; antitussives and expectorants such as dextromethorphan; medicines for peptic ulcer such as dicyclomine and teprenone; antacids such as magnesium oxide and sodium hydrogencarbonate; purgatives such as sennoside; hormone drugs such as kallidinogenase; vitamins such as alfacalcidol, benfotiamine, pyridoxine and cyanocobalamine; calcium drugs such as calcium lactate; hematic medicines such as ticlopidine; medicines for gout such as allopurinol; and medicines for malignant tumors such as tegafur. The medicines and drugs usable in the present invention are by no means limited to them. These medicines and drugs can be used either singly or in combination of two or more of them. Acid-addition salts and base-addition salts of them are also usable. The acid-addition salts include, for example, hydrochloride, sulfate, hydrobromide, methanesulfonate, lactate and carbamate. The base-addition salts include, for example, metal salts such as sodium, potassium, magnesium and calcium salts, ammonium salt and amine-adduct.

The binders which can be contained in the dry gel composition of the present invention include, for example, hydroxypropyl cellulose, hydroxypropyl methylcellulose and polyvinylpyrrolidone.

The dry gel composition of the present invention contains 40% by weight or below, based on the composition, of the medicine which can be orally administered, 3% by weight or above) preferably 10% by weight or above, based on the composition, of the gelling agent and 5% by weight or below, based on the composition, of the binder. In a preferred embodiment of the present invention, the dry gel composition containing pregelatinized starch as the gelling agent contains 40% by weight or below, based on the composition, of the medicine which can be orally administered, 50% by weight or above, preferably 60% by weight or above, based on the composition, of pregelatinized starch as the gelling agent and 5% by weight or below, based on the composition, of the binder.

When 1 part by weight of the dry gel composition of the present invention is mixed with 2 to 15 parts by weight of water, it is swollen, becomes bulky and forms an aqueous gel composition. The aqueous gel composition thus obtained generally has a gruel-like appearance, a self-fluidity and a viscosity of, for example, about 100 to 500 cP. The quantity of water to be added in order to obtain such an aqueous gel composition is suitably selected in the above-described range depending on the power of the gelling agent and the relative amount of the gelling agent to the dry gel composition. For example, when a gelling agent having a strong gelling power such as a mixture of crystalline cellulose and sodium carboxymethyl cellulose (Avicel RC-591NF) is used, the relative amount of the gelling agent to water is reduced, and when a gelling agent having a weak gelling power such as pregelatinized starch is used, the relative amount of the gelling agent to water is increased. Water may be added to the dry gel composition at once or in portions. After the addition of water, the resultant mixture is stirred as immediately as possible for 1 to 2 min until the homogeneous aqueous gel composition has been obtained. The stirring is conducted with a spoon or the like at a temperature of 40° C. or below, preferably at room temperature.

In a preferred embodiment of the present invention, 1 part by weight of the dry gel composition containing at least 50% by weight, based on the composition, of pregelatinized starch is mixed with 6 to 8 parts by weight of water to form a thixotropic aqueous gel composition. The volume of thus swollen aqueous gel composition is 3 to 3.5 times as large as that of the dry gel composition. When the dry gel composition of the present invention is used, it is preferred that the aqueous gel composition having such properties is prepared and administered to the patient. When the quantity of water to be added is smaller than this range, the aqueous gel composition is converted into a substance which looks like dumplings made of rice powder or custard puddings in a few minutes. On the other hand, when it is larger than this range, the resultant aqueous gel composition looks like a thin rice gruel. Both of such aqueous gel compositions prepared from the dry gel composition of the present invention are usable. The custard pudding-like aqueous gel composition is suitable for patients having a relatively normal swallowing function, and the thin rice gruel-like aqueous gel composition is suitable also for tubal feeding. Various aqueous gel compositions can be selectively prepared by controlling the quantity of water to be added depending on the conditions of the patient, which makes the adequate administration of medicine possible.

The dry gel composition of the present invention may contain, in addition to the above-described components, excipients such as lactose and D-mannitol; wetting agents such as glycols, e.g. polyethylene glycol and glycerol; surfactants such as Tween; thickening agents such as sodium carboxymethyl cellulose and guar gum; and carbonates, hydrogencarbonates and organic acids which cause foaming upon addition of water at the time of use. The carbonates and hydrogencarbonates include, for example, potassium carbonate, sodium carbonate, calcium carbonate and sodium hydrogencarbonate, and the organic acids include, for example, citric acid, tartaric acid and malic acid. The foaming agent is preferably used in order to make the aqueous gel bulky. Other additives usable herein include disintegrators, pH adjustors, stabilizers, sweetening agents, flavors and colorants. When a gelling agent having a strong gelling power is used, the quantity thereof is only small and, therefore, it is preferred to increase the proportion of the excipient so as to make the whole composition bulky. When the medicine for the oral administration contained in the dry gel composition of the present invention is bitter, a masking agent for the bitterness can also be used. The masking agents include, for example, glycols such as propylene glycol, glycerol and polyethylene glycol; and taste-improvers such as potassium glutamate and sodium inosinate. Another method can also be employed, wherein a solid bitter medicine is previously finely pulverized and the surface of the particles is coated with a masking agent. Examples of preferred coating agents include water-insoluble ethyl cellulose and hydroxypropyl methylcellulose phthalate.

The dry gel of the present invention is preferably granulated into a granule size of about 100 to 300 μm. The granulation can be conducted by an ordinary method with an organic solvent such as an alcohol, e.g. ethanol or propanol, a chlorinated hydrocarbon, e.g. methylene chloride, a mixture of them, or a mixture of such an organic solvent and water. The granulated dry gel composition of the present invention is advantageous, since when water is added, at the time of use, to the composition, it gels very easily. The dry gel composition usually has a water content of 10% by weight or below before the granulation and 5% by weight or below at the time of the granulation. The dry gel composition of the present invention thus granulated may be further tableted. The tablets of the dry gel composition of the present invention thus prepared are preferred when the dose is to be controlled by counting. When the composition is to be tableted, an excipient and a disintegrator are usable. They are suitably selected by those skilled in the art depending on the components and the use of the dry gel composition of the present invention.

The dry gel of the present invention can be produced by, for example, the following method by means of a high-performance stirring/granulating machine (such as NGSD-350; a product of Daiwa Kakoki) capable of mixing and kneading the powders by rotating blades fixed on a rotating shaft and also capable of granulating by aggregation, shearing, tumbling and grading to form the granules: the starting medicine to be orally administered, a gelling agent such as pregelatinized starch and the excipient are fed into a stirring tank, and they are mixed by rotating the blades of the granulating machine at a rate of about 100 to 200 rpm. The binder is added to the mixture, and the resultant mixture is stirred with the blades rotating at an increased rate of about 300 to 500 rpm to form the granules. The granules thus obtained are dried with an air dryer at, for example, 40° C. for about 5 to 7 hours. The granules are then sieved to obtain the dry gel composition of the present invention. The dry gel composition thus obtained is stable even after storage at 60° C. for two months.

The following Examples will further illustrate the present invention, which by no means limit the invention.

EXAMPLE 1

The dry gel composition of the present invention was produced with a high-performance granulating machine (NGSD-350; a product of Daiwa Kakoki; New gramachine, capacity: 33 l) having two lower scraping blades and two upper flat blades fixed in this order on the rotating shaft in such manner of crossing at sight angles. Predetermined quantities of the medicine to be orally administered and pregelatinized starch were fed into the stirring tank and they were stirred with the blades at 100 rpm for 10 min and then at 200 rpm for additional 10 min. Then the binder was added thereto while the rotation rate was kept at 200 rpm, and thereafter the rotation rate was elevated to 300 rpm while the granulation state was observed. The addition of the binder was completed in 5 min. After the completion of the addition of the binder, the rotation rate was gradually elevated from 300 rpm to 500 rpm. The granulation was completed after about 5 to 8 min, and the granules were recovered. The granules were dried with an air dryer (shelf type) at 40° C. for 5 to 7 hours, and then sieved through a 1000 μm sieve to obtain the dry gel composition of the present invention. The compositions thus obtained are given in the following Table 1.

TABLE 1

| Composition No. | 1 | 2 | 3 | 4 | 5 | 6 | 7 |
|---|---|---|---|---|---|---|---|
| Cinnarizine | 286 g | 286 | 300 | 300 | 300 | — | — |
| Allopurinol | — | — | — | — | — | 600 | 600 |
| Pregelatinized starch | | | | | | | |
| Matsunorin CM[1] | 1,400 g | — | — | 1,440 | — | 1,560 | — |
| Matsunorin W[2] | — | 1,400 | 1,440 | — | 1,440 | — | 1,560 |
| Binder TC-5 "S"[3] | 35 g | 35 | 36 | 36 | 36 | 36 | 36 |
| Lactose 200M[4] | 390 g | 390 | 444 | 444 | 444 | 120 | 120 |
| D-Mannitol | 175 g | 175 | 180 | 180 | 180 | 84 | 84 |
| Composition of binder (for gradulation) Conc. (%) | 7.2 | 7.2 | 7.2 | 7.2 | 7.2 | 7.2 | 7.2 |
| Amount (wt.) of TC-5 "S" | 35 g | 35 | 36 | 36 | 36 | 36 | 36 |
| Anhydrous ethanol | 410 g | 410 | 422 | 422 | 422 | 422 | 422 |
| Water | 41 g | 41 | 42 | 42 | 42 | 42 | 42 |
| Recovery | | | | | | | |
| 1000 μm on | 27 g | 17 | 10 | 29 | 4 | 15 | 5 |
| 1000 μm pass | 2,245 g | 2,268 | 2,394 | 2,354 | 2,406 | 2,376 | 2,385 |
| Granular size distribution [1000 μm pass:sieving method (%) n = 3] | | | | | | | |
| 850 μm on | 1.6 | 1.0 | 1.0 | 2.3 | 0.6 | 1.3 | 0.7 |
| 500 μm on | 9.4 | 6.3 | 5.1 | 11.8 | 4.6 | 8.3 | 4.2 |
| 250 μm on | 12.5 | 9.7 | 8.1 | 16.2 | 7.6 | 12.9 | 7.8 |
| 150 μm on | 41.8 | 32.8 | 30.1 | 40.2 | 29.7 | 40.4 | 18.9 |
| 75 μm on | 31.9 | 45.3 | 49.7 | 26.8 | 51.5 | 33.0 | 58.0 |
| 75 μm pass | 2.7 | 5.0 | 6.0 | 2.7 | 6.0 | 4.2 | 10.4 |

[1]Matsunorin CM: pregelatinized starch from corn starch; a product of Matsutani Chemical Industries Co., Ltd.
[2]Matsunorin W: pregelatinized starch from wheat starch; a product of Matsutani Chemical Industries Co., Ltd.
[3]Binder TC-5 "S": hydroxypropyl methylcellulose; a product of Shin-Etsu Chemical Co., Ltd.,
[4]lactose 200: 200 mesh-passed lactose.

Water was added to each of the compositions shown in Table 1 to obtain a gruel-like aqueous gel composition. The properties of the aqueous gel composition were determined under the following conditions:

Apparatus used: rheometer NRM-120 (a product of Nippon Rheology Kabushiki Kaisha),
Standard solution for calibration of viscometer: JIS Z 9909 JS 200 (Lot 24) (a product of Showa Shell Sekiyu K.K.),
Determination conditions:
  Temperature: 20° C.
  Shear rate: 1800 s$^{-1}$ (100 rpm)
  Program time: 60 s .
  Sample-preparation method: 8, 12, 14 or 16 ml of purified water was added to 2 g of the sample, and the mixture was stirred for 2 min.
  Measurement intervals: after 5 min, 10 min and 60 min.
  Frequency of measurement: continuous repeated measurement (3 times) for each sample.
  Point of time of measurement: The viscosity was determined at the maximum shear rate.

The results are given in the following Tables 2 and 3.

TABLE 2

| Preparation No. | | 1 | |
|---|---|---|---|
| | First | Second | Third |
| 5 min. after | 266 | 264 | 264 |
| 1:6 30 min. after | 288 | 288 | 287 |
| 60 min. after | — | — | — |

| Preparation No. | | 2 | |
|---|---|---|---|
| | First | Second | Third |
| 5 min. after | 306 | 328 | 320 |
| 1:6 30 min. after | 398 | 360 | 331 |
| 60 min. after | 527 | 439 | 392 |

| Preparation No. | | 3 | |
|---|---|---|---|
| | First | Second | Third |
| 5 min. after | 291 | 327 | 322 |
| 1:6 30 min. after | 362 | 342 | 320 |
| 60 min. after | 470 | 410 | 360 |

TABLE 3

| Preparation No. | | 4 | | | 5 | |
|---|---|---|---|---|---|---|
| | First | Second | Third | First | Second | Third |
| 5 min. after | 1492 | 1378 | 1318 | 1151 | 1015 | 921 |
| 1:4 30 min. after | 1268 | 1272 | 1238 | 1171 | 1175 | 1091 |
| 60 min. after | 1068 | 1332 | 1248 | 1228 | 1125 | 1038 |
| 5 min. after | 210 | 208 | 208 | 282 | 310 | 302 |
| 1:6 30 min. after | 224 | 226 | 232 | 362 | 327 | 299 |
| 60 min. after | 306 | 306 | 307 | 429 | 344 | 326 |
| 5 min. after | 117 | 119 | 119 | 132 | 130 | 132 |
| 1:7 30 min. after | 109 | 99 | 93 | 190 | 178 | 174 |
| 60 min. after | 117 | 104 | 100 | 165 | 162 | 157 |
| 5 min. after | 66 | 56 | 53 | 72 | 66 | 65 |
| 1:8 30 min. after | 71 | 59 | 55 | 88 | 85 | 86 |
| 60 min. after | 74 | 59 | 53 | 101 | 94 | 89 |

| Preparation No. | | 6 | | | 7 | |
|---|---|---|---|---|---|---|
| | First | Second | Third | First | Second | Third |
| 5 min. after | 1725 | 1478 | 1375 | 1562 | 1402 | 1272 |
| 1:4 30 min. after | 1368 | 1352 | 1252 | 1378 | 1422 | 1318 |
| 60 min. after | 2137 | 1949 | 1795 | 1445 | 1298 | 1201 |
| 5 min. after | 272 | 272 | 264 | 429 | 391 | 356 |
| 1:6 30 min. after | 259 | 270 | 268 | 563 | 443 | 400 |
| 60 min. after | 379 | 351 | 332 | 725 | 561 | 502 |
| 5 min. after | 138 | 135 | 135 | 256 | 229 | 216 |
| 1:7 30 min. after | 221 | 189 | 178 | 394 | 364 | 341 |
| 60 min. after | 236 | 212 | 202 | 352 | 329 | 254 |
| 5 min. after | 101 | 101 | 101 | 136 | 132 | 135 |
| 1:8 30 min. after | 70 | 55 | 53 | 121 | 118 | 115 |
| 60 min. after | 96 | 73 | 65 | 232 | 184 | 159 |

EXAMPLE 2

The dry gel compositions of the present invention given in the following Table 4 were prepared in the same manner as that of Example 1. Composition No. 17 was prepared by adding low substituted hydroxypropyl cellulose as the disintegrator to the granules prepared as described above and tableting the resultant mixture with an autograph (a product of Shimadzu Corporation) to obtain raw tablets each containing 50 mg of cinnarizine.

EXAMPLE 3

The dry gel compositions of the present invention given in the following Table 5 were prepared in the same manner as that of Example 1. Composition No. 21 was prepared by tableting in the same manner as that for the composition No. 17 to obtain raw tablets each containing 50 mg of cinnarizine.

TABLE 4

| Composition No. | 8 | 9 | 10 | 11 | 12 | 13 | 14 | 15 | 16 | 17 |
|---|---|---|---|---|---|---|---|---|---|---|
| Cinnarizine | 50 mg | 50 mg | 50 mg | 50 mg | 50 mg | 50 mg | 50 mg | 50 mg | 50 mg | 50 mg |
| Pionil 1500[1] | — | 260 mg | — | — | — | — | — | — | — | — |
| Genu gel SWG-J[2] | — | — | 40 mg | — | — | — | — | — | — | 5 mg |
| Locust bean gum | — | — | 80 mg | — | — | — | — | — | — | 10 mg |
| Primojel[3] | — | — | — | 130 mg | — | — | — | — | — | — |
| GENU pectin[4] | — | — | — | — | 120 mg | — | — | — | — | — |
| Guaiacol[5] | — | — | — | — | — | 80 mg | — | — | — | — |
| L-HPC(LH-31)[6] | — | — | — | — | — | — | 40 mg | — | — | — |
| L-HPC(LH-21)[6] | — | — | — | — | — | — | — | — | — | 100 mg |
| Tragacanth powder | — | — | — | — | — | — | — | 60 mg | — | — |
| Bentonite | — | — | — | — | — | — | — | — | 200 mg | — |
| Sodium Carmellose | — | — | — | — | — | — | 40 mg | — | 40 mg | — |
| Calcium lactate | — | — | — | — | 10 mg | — | — | — | — | — |
| Lactose (200M) | 204 mg | 54 mg | 124 mg | 114 mg | 114 mg | 184 mg | 184 mg | 204 mg | 64 mg | 100 mg |
| D-Mannitol | 100 mg | 30 mg | 100 mg | 100 mg | 100 mg | 80 mg | 80 mg | 80 mg | 40 mg | 127 mg |
| Avicel RC-591NF | 40 mg | — | — | — | — | — | — | — | — | — |
| TC-5 "S"[7] | 6 mg | 6 mg | 6 mg | 6 mg | 6 mg | 6 mg | 6 mg | 6 mg | 6 mg | — |
| HPC "L"[8] | — | — | — | — | — | — | — | — | — | 8 mg |
| Total | 400 mg | 400 mg | 400 mg | 400 mg | 400 mg | 400 mg | 400 mg | 400 mg | 400 mg | 400 mg |

[1] Sodium starch phosphate
[2] Carrageenin
[3] Carboxymethylated starch
[4] LM pectin
[5] Guar gum
[6] Low substituted hydroxypropyl cellulose
[7] Hydroxypropyl methylcellulose
[8] Hydroxypropyl cellulose

TABLE 5

| Composition No. | 18 | 19 | 20 | 21 | 22 | 23 | 24 | 25 | 26 | 27 | 28 | 29 |
|---|---|---|---|---|---|---|---|---|---|---|---|---|
| Cinnarizine | 12.5 | 12.5 | 12.5 | 12.5 | 12.5 | 12.5 | 12.5 | 12.5 | 12.5 | 12.5 | 50 | 50 |
| Avicel RC-591NF | 32.5 | — | — | — | — | — | — | — | — | — | — | — |
| Pionil 1500[1] | — | 35.0 | — | — | — | — | — | — | — | — | — | — |
| Genu gel SWG-J[2] | — | — | 3.75 | 2.50 | — | — | — | — | — | — | — | — |
| Locust bean gum | — | — | 7.50 | 5.00 | — | — | — | — | — | — | — | — |
| Primojel[3] | — | — | — | — | 47.5 | — | — | — | — | — | — | — |
| GENU pectin[4] | — | — | — | — | — | 30.0 | — | — | — | — | — | — |
| Calcium lactate | — | — | — | — | — | 2.50 | — | — | — | — | — | — |
| Guaiacol[5] | — | — | — | — | — | — | 25.0 | — | — | — | — | — |
| L-HPC(LH-31)[6] | — | — | — | — | — | — | — | 17.5 | — | — | — | — |
| Sodium Carmellose | — | — | — | — | — | — | — | 17.5 | 10.0 | — | — | — |
| Bentonite | — | — | — | — | — | — | — | — | 60.0 | — | — | — |
| Tragacanth powder | — | — | — | — | — | — | — | — | — | 20.0 | — | — |
| Matsunorin CM | — | — | — | — | — | — | — | — | — | — | 240 | — |
| Matsunorin W | — | — | — | — | — | — | — | — | — | — | — | 240 |
| L-HPC (LH-21)[6] | — | — | — | 25.0 | — | — | — | — | — | — | — | — |
| Lactose (200M) | 33.5 | 31.0 | 54.75 | 33.5 | 18.5 | 33.5 | 20.0 | 31.0 | 6.00 | 46.00 | 74 | 74 |
| D-Mannitol | 20.0 | 20.0 | 20.0 | 20.0 | 20.0 | 20.0 | 20.0 | 20.0 | 10.0 | 20.0 | 30 | 30 |
| TC-5 "S"[7] | 1.50 | 1.50 | 1.50 | 1.50 | 1.50 | 1.50 | 1.50 | 1.50 | 1.50 | 1.50 | 6 | 6 |
| Total | 100 mg | 100 mg | 100 mg | 100 mg | 100 mg | 100 mg | 100 mg | 100 mg | 100 mg | 100 mg | 400 mg | 400 mg |

[1] Sodium starch phosphate
[2] Carrageenin
[3] Carboxymethylated starch
[4] LM pectin
[5] Guar gum
[6] Low substituted hydroxypropyl cellulose of substitution
[7] Hydroxypropyl methylcellulose The properties of each of aqueous gel compositions obtained by adding water to the dry gel compositions of the present invention given in Table 4 in the same manner as that of Example 1 were determined after 60 min to obtain the results given in the following Table 6.

TABLE 6

| Composition No. | Ratio | First | Second | Third |
|---|---|---|---|---|
| 8 | 1:2 60 min. after | 162 | 151 | 146 |
| 9 | 1:10 60 min. after | 481 | 454 | 450 |
| 10 | 1:15 60 min. after | 184 | 201 | 244 |
| 11 | 1:3 60 min. after | 1540 | 929 | 530 |
| 12 | 1:5 60 min. after | 793 | 787 | 772 |
| 13 | 1:5 60 min. after | 389 | 281 | 253 |

TABLE 6-continued

| Composition No. | Ratio | | First | Second | Third |
|---|---|---|---|---|---|
| 14 | 1:3 | 60 min. after | 551 | 568 | 603 |
| 15 | 1:5 | 60 min. after | 173 | 177 | 166 |
| 16 | 1:3 | 60 min. after | 897 | 800 | 783 |
| 17 | 1:5 | 60 min. after | 357 | 352 | 358 |

Industrial Usability

When the dry gel composition of the present invention is mixed with a predetermined quantity of water, a homogeneous gruel-like aqueous gel composition is obtained. Even aged people having a weak swallowing function can easily swallow the aqueous gel composition thus prepared, without improper sucking into their tracheas. Thus, the dry gel composition of the present invention is very useful in their medical care. Another characteristic feature of the present invention is that the aqueous gel composition can be prepared in a short time by an extremely simple operation at the time of use.

What is claimed is:

1. A dry gel composition comprising 40% by weight or below, based on the whole composition, of a medicine which can be orally administered, 3% by weight or above of a gelling agent comprising pregelatinized starch and 5% by weight or below of a binder, which composition is capable of forming an aqueous gel composition having viscosity of about 100 to 500 cP and having a consistency of gruel, upon mixing with 2 to 15 parts by weight of water per part by weight of the composition at a temperature of 40° C. or below, wherein the medicine which can be orally administered is cinnarizine or allopurinol.

2. The composition according to claim 1 wherein the gelling agent is a substance capable of forming a gel upon stirring with water in an amount of not larger than the maximum absorption at a temperature of 40° C. or below.

3. The composition according to claim 2 wherein the gelling agent is thixotropic.

4. The composition according to claim 1 wherein an aqueous gel composition having a consistency of gruel, obtained by mixing 1 part by weight of the composition with 6 to 8 parts by weight of water at a temperature of 40° C. or below has a self-fluidity and a viscosity of 100 to 500 cP.

5. The composition according to claim 4 wherein the aqueous gel composition is thixotropic.

6. The composition according to claim 1, which has been granulated.

7. A dry gel composition containing 40% by weight or below of a medicine which can be orally administered, 50% by weight or above of pregelatinized starch and 5% by weight or below of a binder, which composition is capable of forming an aqueous gel composition having a viscosity of about 100 to 500 cP and having a consistency of gruel, upon mixing with 6 to 8 parts by weight of water per part by weight of the composition at a temperature of 40° C. or below.

8. The composition according to claim 7, which contains 60% by weight or above of pregelatinized starch.

9. The composition according to claim 7 wherein an aqueous gel composition obtained by mixing 1 part by weight of the composition with 6 to 8 parts by weight of water at a temperature of 40° C. or below has a self-fluidity and a viscosity of 100 to 500 cp.

10. The composition according to claim 9 wherein the aqueous gel is thixotropic.

11. The composition according to claim 7, which has been granulated.

12. The composition according to claim 7, wherein the medicine which can be orally administered is cinnarizine or allopurinol.

* * * * *